United States Patent
Apffel et al.

(10) Patent No.: US 6,278,110 B1
(45) Date of Patent: Aug. 21, 2001

(54) ORTHOGONAL ION SAMPLING FOR APCI MASS SPECTROMETRY

(75) Inventors: James A. Apffel, Palo Alto; Mark H. Werlich, Santa Clara; James L. Bertsch, Palo Alto; Paul C. Goodley, Cupertino, all of CA (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/030,676

(22) Filed: Feb. 25, 1998

Related U.S. Application Data

(63) Continuation of application No. 08/794,248, filed on Feb. 3, 1997, now Pat. No. 5,750,988, which is a continuation of application No. 08/555,250, filed on Nov. 8, 1995, now abandoned, which is a continuation-in-part of application No. 08/273,250, filed on Jul. 11, 1994, now Pat. No. 5,495,108.

(51) Int. Cl.$^7$ .................................................. H01J 44/26
(52) U.S. Cl. ........................................................ 250/288
(58) Field of Search ............................... 250/288, 288 A, 250/281, 282

(56) References Cited

U.S. PATENT DOCUMENTS 5,495,108 * 2/1996 Apffel, Jr. et al. .................... 250/288
5,750,988 * 5/1998 Apffel et al. ......................... 250/288

* cited by examiner

*Primary Examiner*—Kiet T. Nguyen

(57) ABSTRACT

A method and apparatus wherein a plurality of electric fields and of orthogonal spray configurations of vaporized analyte are so combined as to enhance the efficiency of analyte detection and mass analysis. The invention provides reduced noise and increased signal sensitivity in both API electrospray and APCI operating modes.

4 Claims, 5 Drawing Sheets

ORTHOGONAL ION SAMPLING FOR APCI MASS SPECTROMETRY

INTRODUCTION

This application is a continuation of U.S. patent application Ser. No. 08/794,248 filed Feb. 3, 1997, now U.S. Pat. No. 5,750,988, which in turn is a continuation of U.S. patent application Ser. No. 08/555,250, filed Nov. 8, 1995, now abandoned, which in turn is a continuation-in-part of U.S. patent application Ser. No. 08/273,250, filed Jul. 11, 1994, now U.S. Pat. No. 5,495,108, issued Feb. 27, 1996.

The invention relates to a method and apparatus for obtaining improved signal relative to noise without loss of ion collection efficiency for use in mass spectrometry, including LC/MS (liquid chromatography/mass spectrometry), especially as regards the technique of generating analyte ions known as Atmospheric Pressure Chemical Ionization (APCI).

BACKGROUND

Liquid chromatography and mass spectrometry have proven powerful analytical tools in identifying molecular components of our world. Liquid chromatography is a fundamental separation technique. Mass spectrometry is a means of identifying "separated" components according to their characteristic "weight" or mass-to-change ratio. The liquid effluent from LC is prepared for ionization and analysis using any of a number of techniques. A common technique, electrospray, involves spraying the sample into fine droplets.

Early systems for electrospray LC/MS utilized flow splitters that divided the HPLC (high performance liquid chromatography) column effluent. As a result of the effluent splitting, only a small portion, typically 5–50 micro liters per minute, was introduced into the "spray chamber". The bulk of the column effluent did not enter the spray chamber but went directly to a waste or fraction collector. Because electrospray/mass spectrometry (ES/MS) generally provides a concentration sensitive detector, it was not necessary to analyze the entire column effluent flow to obtain sensitive results. Results obtained by splitting are comparable in sensitivity to those obtained by introduction of the entire column effluent flow into the spray chamber (assuming equal charging and sampling efficiencies).

Such low flow rates enabled generation of an electrosprayed aerosol solely through the manipulation of electrostatic forces. However, the use of flow splitters gained a bad reputation due to potential plugging problems and poor reproducibility.

Newer electrospray systems generate a charged or ionized aerosol through the combination of electrostatic forces and some form of an assisted nebulization. Nebulization is the process of breaking a stream of liquid into fine droplets. Nebulization may be "assisted" by a number of means, including but not limited to pneumatic, ultrasonic or thermal assists. The assisted nebulization generates an aerosol from the HPLC column effluent, while electric fields induce a charge on the aerosol droplets. The charged aerosol undergoes an ion evaporation process whereby desolvated analyte ions are produced. Ideally, only the desolvated ions enter the mass spectrometer for analysis.

A challenge in any assisted nebulizer system is designing the vacuum system leading to the mass spectrometer such that desolvated ions enter, but relatively large solvated droplets present in the electrosprayed aerosol are prevented from entering. Several design approaches are currently in use, but none has solved all the challenges. None of the assisted nebulization methods currently practiced provide reliable sensitivity along with robust instrumentation.

In conventional electrospray/nebulization mass spectrometry systems, the electrosprayed aerosol exiting from the nebulizer is sprayed directly towards the sampling orifice or other entry into the vacuum system. That is, the electrosprayed aerosol exiting from the nebulizer and entry into the vacuum system are located along a common central axis, with the nebulizer effluent pointing directly at the entry into the vacuum system and with the nebulizer being considered to be located at an angle of zero (0) degrees relative to the common central axis.

One previous approach directed at improving performance adjusts the aerosol to spray "off-axis". That is, the aerosol is sprayed "off-axis" at an angle of as much as 45 degrees with respect to the central axis of the sampling orifice. In addition, a counter current gas is passed around the sampling orifice to blow the solvated droplets away from the orifice. The gas velocities typically used generate a plume of small droplets. Optimal performance appears to be limited to a flow rate of 200 microliters per minute or lower.

In another system, an aerosol is generated pneumatically and aimed directly at the entrance of a heated capillary tube; the heated capillary exits into the vacuum system. Instead of desolvated ions entering the capillary, large charged droplets are drawn into the capillary and the droplets are desolvated while in transit. The evaporation process takes place in the capillary as well. Exiting the capillary in a supersonic jet of vapor, the analyte ions are subsequently focused, mass analyzed and detected.

This system has several disadvantages and limitations, including sample degradation, re-clustering, and loss of sensitivity. Sensitive samples are degraded due to the heat. In the supersonic jet expansion exiting the capillary, the desolvated ions and vapor may recondense resulting in solvent clusters and background signals. While these clusters may be re-dissociated by collisionally induced processes, this may interfere in identification of structural characteristics of the analyte samples. The large amount of solvent vapor, ions and droplets exiting the capillary require that the detector be arranged substantially off-axis with respect to the capillary to avoid noise due to neutral droplets striking the detector. Removing the large volume of solvent entering the vacuum system requires higher capacity pumps.

Still another system generates the electrosprayed aerosol ultrasonically, uses a counter current drying gas, and most typically operates with the electrosprayed aerosol directed at the sampling capillary. Several serious disadvantages plague this configuration. The optimal performance is effectively limited to less than five hundred (500) microliters per minute. Adequate handling of the aqueous mobile phase is problematic. Furthermore, the apparatus is complex and prone to mechanical and electronic failures.

In another commonly used system, a pneumatic nebulizer is used at substantially higher inlet pressures (as compared with other systems). This results in a highly collimated and directed electrosprayed aerosol. This aerosol is aimed off-axis to the side of the orifice and at the nozzle cap. Although this works competitively, there is still some noise which is probably due to stray droplets. The aerosol exiting the mobilizer has to be aimed carefully to minimize noise while maintaining signal intensity; repeated and tedious adjustments are often required.

While the techniques are varied with respect to the type of nebulization assist, techniques can be broadly characterized along the lines of what process is used for accomplishing ionization of the analyte. Atmospheric Pressure Ionization—Electrospray (API-ES or ES herein) and Atmospheric Pressure Chemical Ionization (APCI) differ in the ionization mechanism. Each technique is suited to complementary classes of molecular species.

The techniques are, in practice, complementary owing to different strengths and weaknesses. Briefly, API-ES is generally concentration dependent (that is to say, higher concentration equals better performance), and performs well in the analysis of moderately to highly polar molecules. It works well for large, biological molecules and pharmaceuticals, especially molecules that ionize in solution and exhibit multiple charging. API-ES also performs well for small molecules, provided the molecule is fairly polar. Low flow rates enhance performance. APCI, on the other hand, performs with less dependence on concentration and performs better on smaller non-polar to moderately polar molecules. Higher flow rates enhance performance.

At the most fundamental level, APCI involves the conversion of the mobile phase and analyte from the liquid to the gas phase and then the ionization of the mobile phase and analyte molecules. APCI is a soft ionization technique that yields charged molecular ions and adduct ions. APCI, as implemented in the hardware described herein, actually includes several distinct ionization processes, with the relative influence of each process dependent on the chemistry of the mobile phase and the analyte. What is desired is an assisted nebulization LC/MS configuration for APCI that operates in a complementary range of flow rates as does API-ES. What is further needed and wanted from the practitioner's point of view is a mass spectrometry apparatus easily and interchangeably configurable for operation in either API-ES or APCI mode with increased sensitivity in both operating modalities. What is further desired is a robust instrumentation that provides sensitive results without constant calibrating or other process interruptive maintenance procedures.

SUMMARY OF INVENTION

The invention relates to an apparatus for converting a liquid solute sample into vaporized and ionized molecules comprising:

- a first passageway having a center axis, an orifice for accepting a liquid solute sample, an interior chamber within which the liquid solute sample is converted into vaporized molecules, and an exit for discharging the vaporized molecules;
- a point charge voltage source having the point arranged adjacent to the first passageway exit which ionizes the vaporized molecules into ionized molecules;
- an electrically conductive housing connected to a second voltage source and having an opening arranged adjacent to the first passageway exit wherein the ionized molecules formed by the point charge voltage source are interposed between the point charge voltage source and the housing;
- a second passageway arranged within the housing adjacent to the opening and connected to a third voltage source, the second passageway having a center axis, an orifice for receiving ionized molecules and an exit, wherein the center axis of the second passageway is arranged in transverse relation to the center axis of the first passageway such that the ionized molecules move laterally through the opening in the housing and thereafter pass into the second passageway under the influence of electrostatic attraction forces generated by the second and third voltage sources.

The invention provides the capability of ionizing effluent from conventional high performance liquid chromatography (HPLC) at flow rates of greater than one (1) ml/minute without flow splitting. The invention provides that ionization may be accomplished in a variety of manners, including atmospheric pressure chemical ionization (APCI) as well as atmospheric pressure ionization electrospray (API-ES). The invention further provides that desolvated ions be separated from comparatively large volumes of vaporized aerosol from the column effluent, and then, while keeping out as much of the aerosol as possible, introducing the desolvated ions into the vacuum system for mass detection and analysis. The invention provides the capability of separating desolvated ions from the large volumes of vapor, and directing the desolvated ions from the ionization chamber (typically operating at atmospheric pressure) to the mass spectrometer (MS) (operating at $10^{-6}$ to $10^{-4}$ torr). The inventive separation capability preserves instrument sensitivity because the maximum amount of analyte (in the form of desolvated ions) is introduced into vacuum system to be mass analyzed and detected. Furthermore, the inventive sensitivity is preserved without overwhelming the vacuum system with large volumes of liquid droplets or vapor.

Orthogonal ion sampling according to the present invention allows more efficient enrichment of the analyte by spraying the in the electrosprayed aerosol past a sampling orifice, while directing the solvent vapor and solvated droplets in the electrosprayed aerosol away from the ion sampling orifice such that they do not enter the vacuum system.

The noise level in an apparatus configured according to the present invention is reduced by as much as five fold over current systems, resulting in increased signal relative to noise, and hence achieving greater sensitivity. Performance is simplified and the system is more robust because optimization of the position, of the first passageway gas flow and voltages show less sensitivity to small changes. The simplified performance and reduced need for optimization also result in a system less dependent upon flow rate and mobile phase conditions. The reduced need for optimization extends to changing mobile phase flow rates and proportions. Practically speaking, an apparatus configured to employ the inventive system can be run under a variety of conditions without adjustment.

Another benefit of the invention taught herein is simplified waste removal owing to the fact that the electrosprayed aerosol can be aimed directly at a waste line and be easily removed from the system. Furthermore, the present invention provides the option of eliminating high voltage elements with no loss of sensitivity.

DETAILED DESCRIPTION OF THE INVENTION

Figure 1:
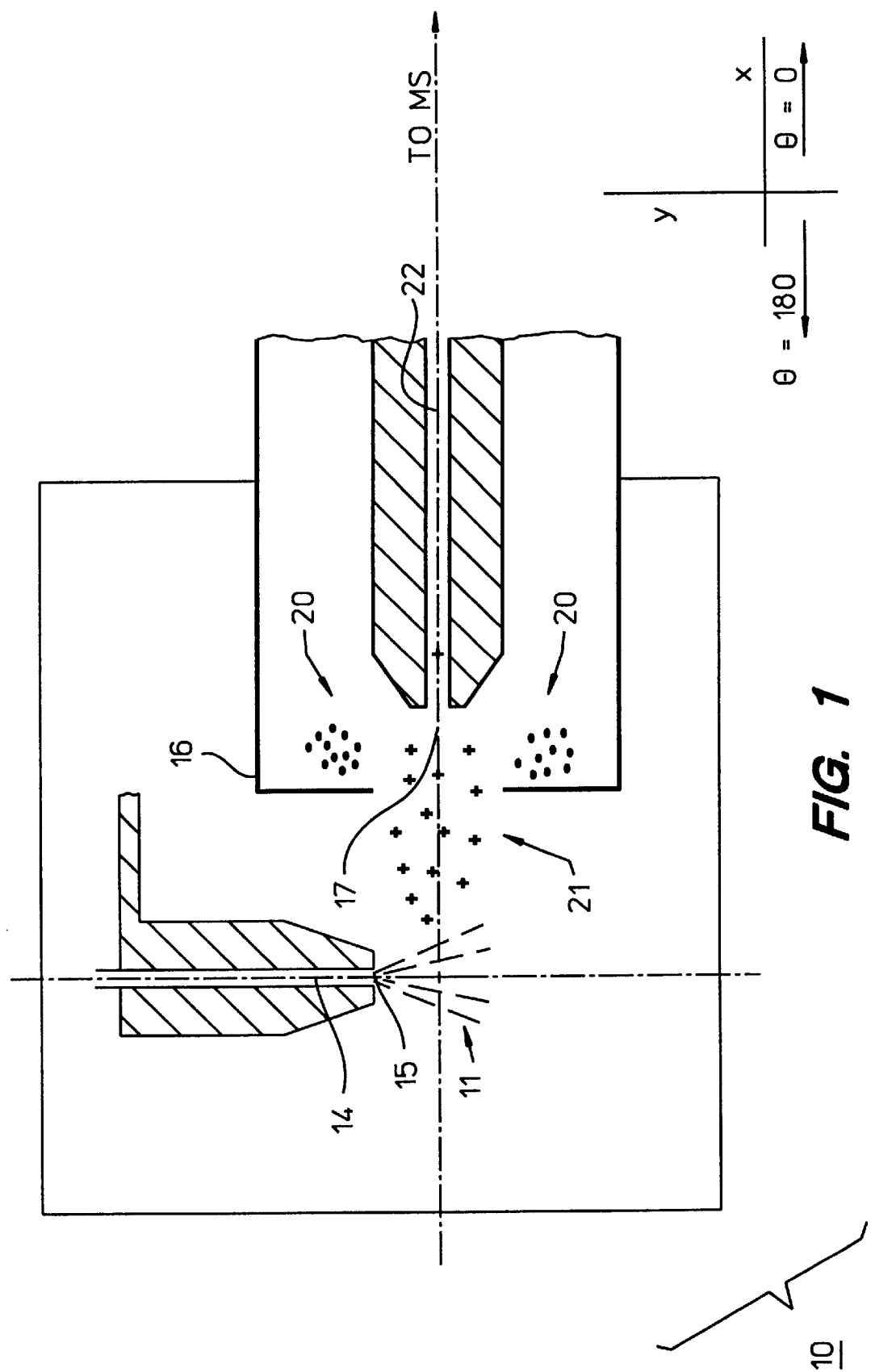
FIG. 1 is a representation of an API-ES apparatus according to the present invention.

FIG. 1 depicts an apparatus 10 configured according to the current invention. As in conventional sample introduction, a liquid sample is conducted through a nebulizer and into a first passageway 14, exiting via a second 15 (the exit of the first passageway 14) under conditions which create a vapor of charged droplets or electrosprayed aerosol 11. The invention provides a rather different electrospray particle transport as compared with conventional electrospray processes. FIG. 1 depicts the transport of the electrospray droplets from the exit 15 of the first passageway 14, through the distance to the opening to or orifice 17 of a second passageway 22, and entering the second passageway 22 where the center axis of the exiting electrosprayed aerosol 11 and the center axis of the second passageway 22 is between 75 and 105 degrees, with respect to each other. The angle may be greater than 105 and, in principle, as great as 180 degrees; in practice, best results have been obtained at settings at or near 90 degrees. As shown in FIG. 1, the angle θ defines the location of the first passageway 14, that is, the nebulizer or other source of electrosprayed aerosol 11, relative to the second passageway 22, that is, the entry into the vacuum system. The angle θ is considered to be zero (0) degrees when the exit 15 for the electrosprayed aerosol 11 and the center axis of the first passageway 14 are pointing directly at the entrance 17 and the center axis of the second passageway 22. The angle θ is considered to be 180 degrees when the exit 15 for the electrosprayed aerosol 11 and the center axis of the first passageway 14 are pointing directly away from the entrance 17 and the center axis of the second passageway 22.

The charged droplets forming the electrosprayed aerosol are electrostatically attracted laterally across a gap between the exit 15 of the first passageway 14 into the opening 17 of the second passageway 22. The electrostatic attraction is generated by attaching voltage sources to components of the apparatus. A first voltage source (not shown) is connected to a housing 16 which houses the second passageway 22. The housing 16 is not necessarily an enclosure but may be any shape that can act as a guide for the ions and can support fluid dynamics of a drying gas (discussed below). A second voltage source (not shown) is connected to the second passageway 22. The first passageway 14 is generally kept at ground potential.

In the course of crossing the gap and approaching the opening 17 to the second passageway 22, especially after passing through an opening 21 in the housing 16 containing the second passageway 22, the electrosprayed aerosol is subjected to the cross flow of a gas 20—a condition that operates to remove solvent from the droplets, thereby leaving charged particles or ions. The ions are amenable to analysis by operation of an analytic instrument capable of detecting and measuring mass and charge of particles such as a mass spectrometer (not shown). The second passageway 22 exits into the mass spectrometer or equivalent instrument.

A standard electrospray MS system (HP 5989) with a pneumatic nebulizer provides the base structure. A spray box 12 of plexiglass or some other suitable material for preventing shock and containing noxious vapors replaces the standard spray chamber.

Within the spray box 12, the nebulizer and first passageway 14 may be arranged in a variety of configurations, so long as the distances between the separate high voltage sources are sufficient to prevent discharges. Additional surfaces at high voltage may be used to shape the electrical fields experienced by the electrosprayed aerosol. In the embodiment depicted in FIG. 1, the system includes a drying gas 20 to aid desolvation and prevent droplets in the electrosprayed aerosol 11 from entering the orifice 17 of the second passageway 22 and the vacuum system (not shown). An alternate embodiment could include a heated capillary as the second passageway 22 in an internal source off-axis geometry, such that the capillary is off-axis with respect to quadrupole and detector components.

The positive ion configuration shown in FIG. 1 typically has the second voltage source set approximately at −4.5 kV, the first voltage source at −4 kV, and the first passageway 14 (wherein the passageway is comprised of a needle) set at relative ground. Gas, usually nitrogen at nominally 200 to 400 degrees Centigrade and approximately ten standard liters per minute, is typically used as a cross flow drying gas, although other gases can be used. The drying gas 20 flows across the aperture at approximately 90 degrees to the axis of the charged molecules in the electrosprayed aerosol.

The term "passageway", as used herein with respect to the second passageway means "ion guide" in any form whatsoever. It is possible that the passageway is of such short length relative to the opening diameter that it may be called an orifice. Other ion guides, including capillaries, which are or may come to be used, can operate in the invention. The configurations herein are not meant to be restrictive, and those skilled in the art will see possible configurations not specifically mentioned here but which are included in the teaching and claims of this invention.

Figure 5:
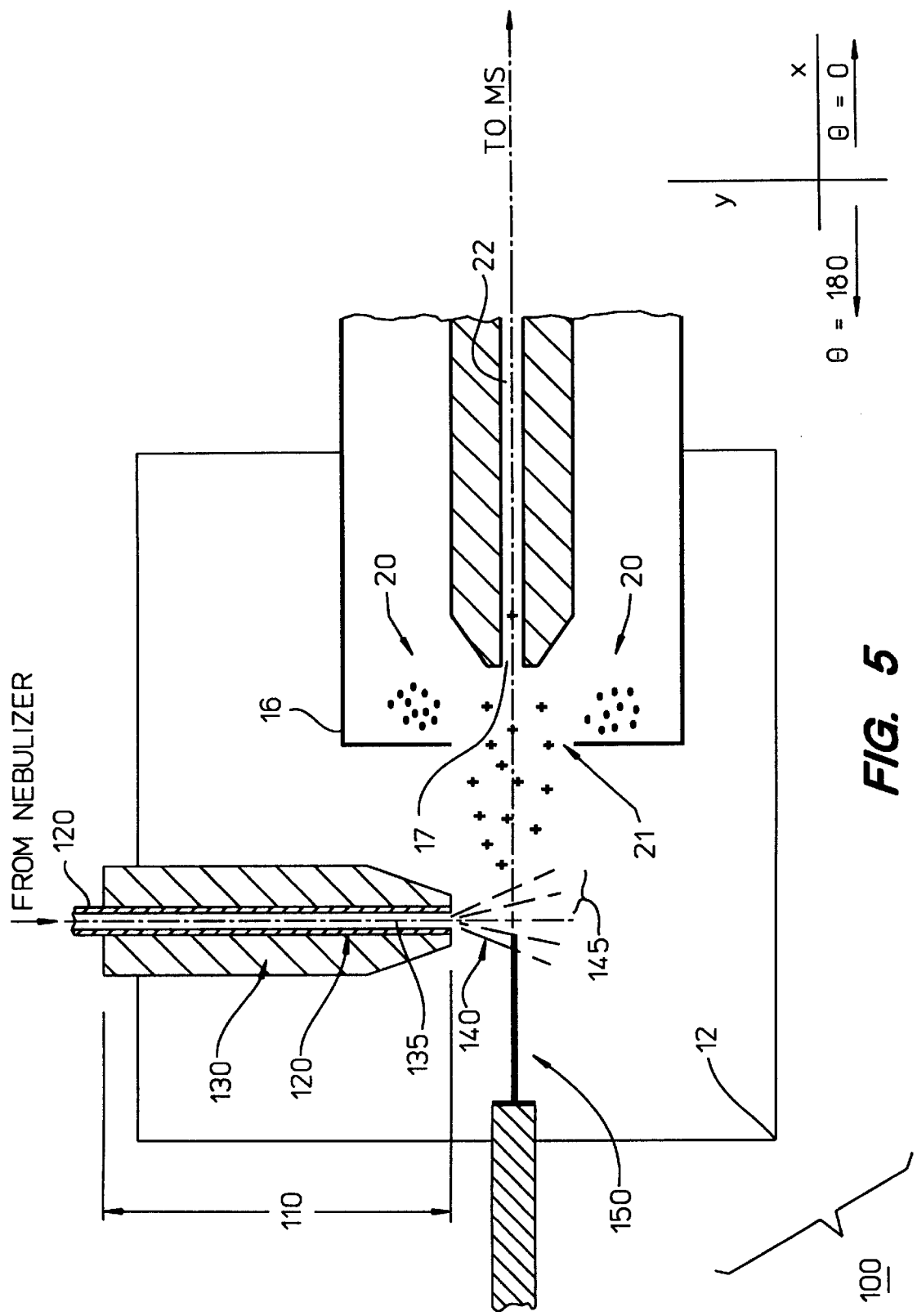
FIG. 5 is a representation of an APCI embodiment according to the present invention.

FIG. 5 illustrates the inventive apparatus as embodying and configured for APCI. As can readily be observed by even a quick perusal of the FIG. 1 and FIG. 5 set side by side, the invention provides that embodiments for API-ES and APCI share much of the same hardware. It is apparent to one of average skill in the art that the configurations depicted herein, as well as many suggested by the illustrative examples, can be adopted interchangeably with relatively straightforward modification of input/output interfaces. FIG. 5 references elements common to FIG. 1 through use of the same numerical identification. By way of background, classical APCI is a multi step process involving the steps of:

1) nebulization of the mobile phase and analyte (breaking into droplets);
2) vaporization of the droplets;
3) ionization of the mobile phase molecules by electrons from the charge source generating a corona discharge;
4) ionization of the analyte molecules by the mobile phase ions.

FIG. 5 depicts an apparatus 100 configured according to the current invention. The sample is nebulized (not shown) by any of number of known nebulization methods, and the resultant droplets proceed into and through a vaporization chamber 110. The vaporization chamber 110 is formed by a capillary or other tube-like structure 120 composed of glass or ceramic or other suitable material. The tube-like structure 120 is subjected to controlled heating through close association with a heating device 130. In the preferred embodiment, both the tube-like structure 120 and the heating device 130 are of a length of several or more inches, the length being determined by the extent to which the heating device 130 is effectively insulated and, being insulated, how effectively the conditions in the vaporization chamber interior 135 promote ionization of the solvent molecules.

The vaporization chamber exit 140 allows the solvent and analyte droplets in the aerosol to pass into an intervening space or gap 145. The molecules typically form a corona (not depicted) at this stage. Because the vaporization chamber is typically at ground, potential the exiting molecules "see" a relatively large charge (either negative or positive) from a charge source 150. The charge source 150 is a point charge (a needle) in the preferred embodiment and the charge source is positioned so as to optimally induce charge transfer among the molecules collected in the gap 145. At this point, APCI takes place: the large charge results in the solvent droplets ionizing and subsequently ionizing the analyte droplets. Once formed, the analyte ions are electrostatically attracted to a complementary (either positive or negative) charge from a voltage source (not shown) applied to the housing 16 of a second passageway 22 which leads to the mass analyzer (not shown) and a stronger relative charge from a voltage source (not shown) applied to the second passageway 22 itself, thereby attracting the analyte ions into the second passageway 22 through the opening 17 thereto.

The orientation angle θ defining the location of the vaporization chamber exit 140 relative to the second passageway 22 is between 75 and 105 degrees. The angle may be greater that 105 degrees; in principle, it may be as great as 180 degrees. However, best results have been obtained at angles at or near 90 degrees. (As shown in FIG. 5, the angle θ which defines the location of the vaporization chamber exit 140 is measured with respect to the center axis defined by the second passageway 22, that is, the entry into the vacuum system. The angle θ is considered to be zero (0) degrees when the vaporization chamber exit 140 and the center axis of the vaporization chamber 110 are pointing directly at the entrance 17 and the center axis of the second passageway 22. The angle θ is considered to be 180 degrees when the vaporization chamber exit 140 and the center axis of the vaporization chamber 110 are pointing directly away from the entrance 17 and the center axis of the second passageway 22.) The vaporization chamber 110 is generally kept at ground potential.

In the preferred embodiment, an HP G1075A APCI accessory accomplishes nebulization as mobile phase and analyte are sprayed out of a small needle. The concentric flow of nebulizing gas tears the stream of liquid into fine droplets in the aerosol. A heated tube in the APCI Accessory vaporizes the droplets of mobile phase and analyte as the droplets pass through the tube. The temperature of the tube is adjustable relative to the volatility of the mobile phase (low volatility indicates need for higher temperature). The selected temperature must substantially complete vaporization without thermally degrading the analyte.

After being vaporized, the mobile phase molecules ionize and subsequently react with and ionize the analyte molecules. The analyte ions thus produced are subject to the separation and direction afforded by the orthospray invention as taught herein.

EXAMPLES

A number of different configurations have been proven possible. Examples of certain tested configurations follow.

Figure 2:
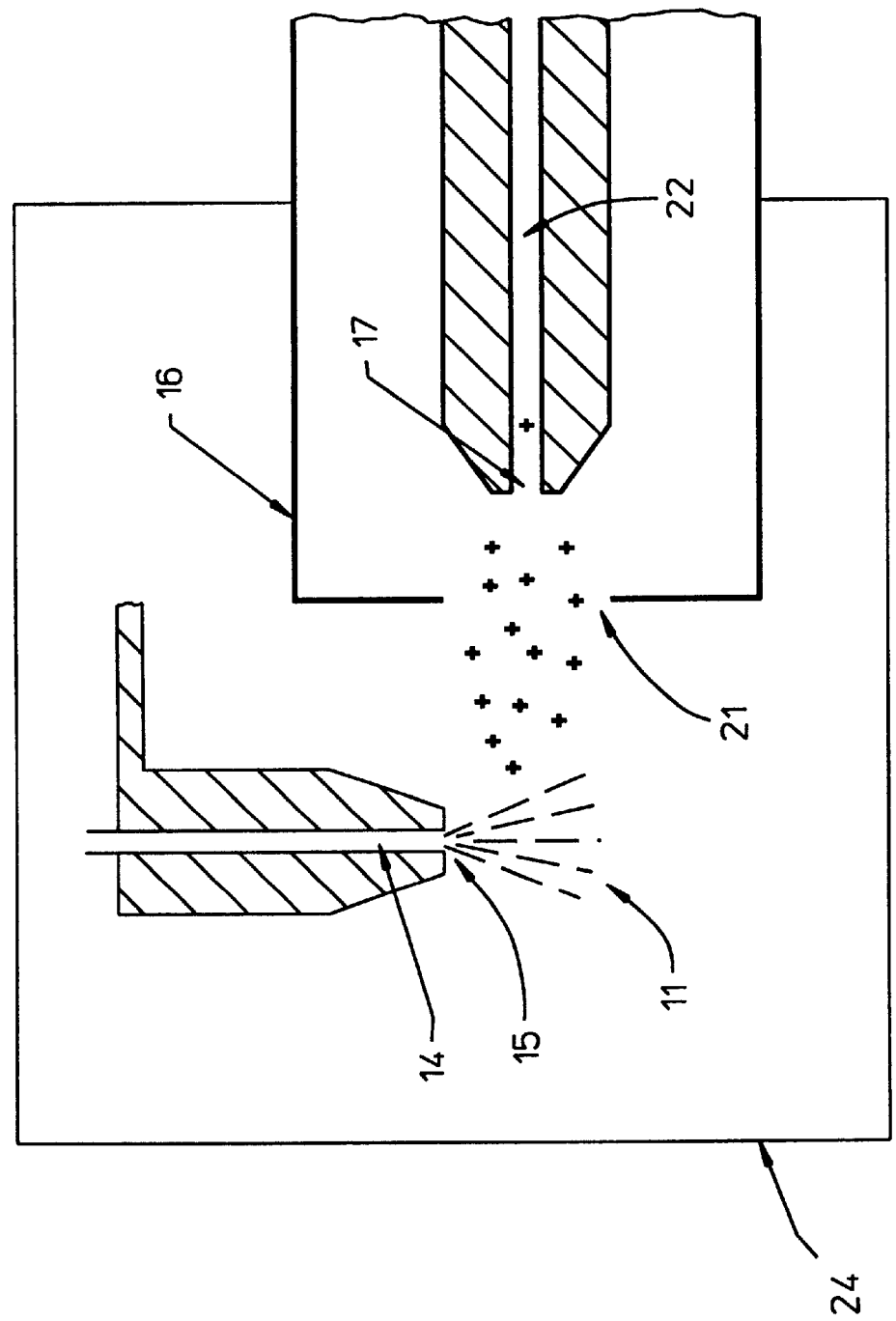
FIG. 2 is a representation of an alternate embodiment of an apparatus according to the present invention.
Figure 3:
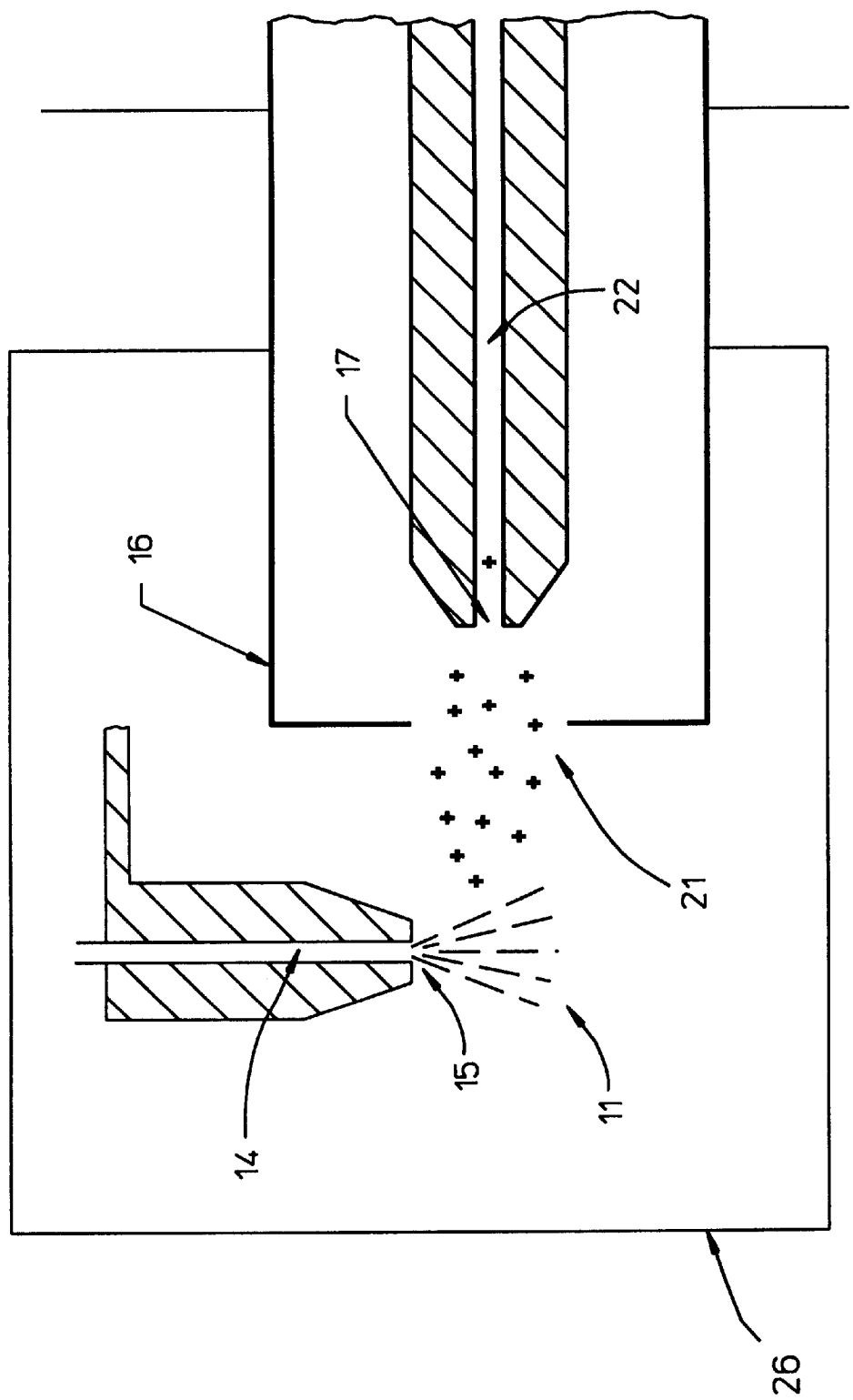
FIG. 3 is a representation of an alternate embodiment of an apparatus according to the present invention.
Figure 4:
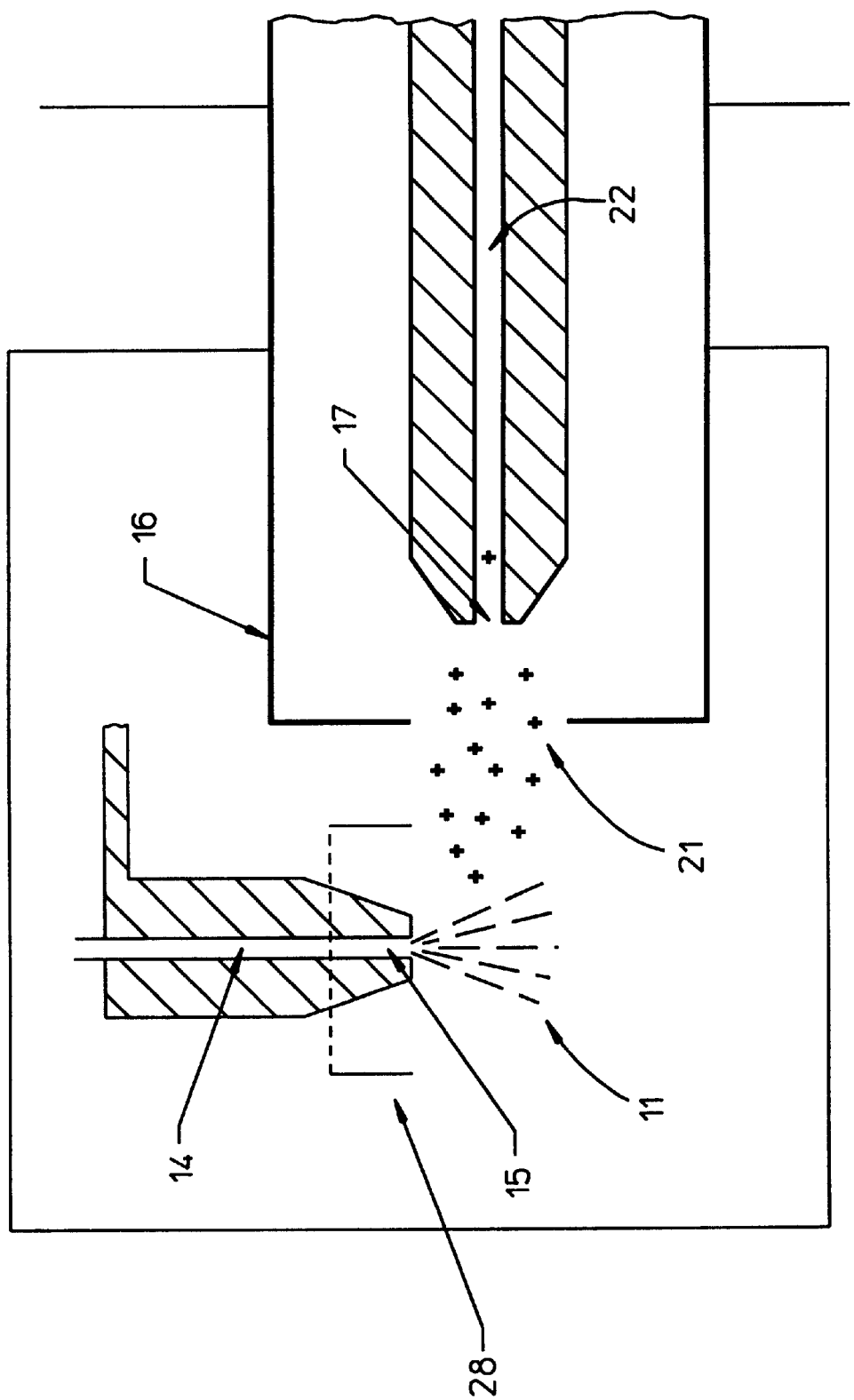
FIG. 4 is a representation of an alternate embodiment of an apparatus according to the present invention.

FIG. 2 shows a configuration of the invention in which a third voltage source, a plate 24, is positioned beside the exit 15 of the first passageway 14 and distal to the side near to which the first voltage source, the opening 21 in the housing 16, and the opening 17 to the second passageway 22 are positioned. The plate 24 runs a positive voltage relative to the charge on the housing 16. Experiments show the electrosprayed aerosol "sees" a mean voltage between the plate 24 and the charged housing 16. Results suggest that the repeller effect may be captured and ion collection yield increased by careful sculpting of both the electric field and the gas flow patterns.

FIG. 3 shows a two voltage source system as in FIG. 2 with the addition of a grounded spray chamber 26. The spray chamber 26 operates to contain the electrosprayed aerosol and route condensed vapor to waste.

FIG. 4 shows the addition of a ring-shaped electrode 28 encircling the electropsayed aerosol exiting from the needle or first passageway 14 at ground, with all of the elements configured as in FIG. 3. The ring-shaped electrode 28 induces a charge in the droplets by virtue of the potential difference in charge between the droplets and the ring-shaped electrode 28. Other potentials in the system can be used to direct the sampling of ions.

FIG. 5 illustrates APCI embodiment of the invention taught herein. The typical relative voltages are: source 150 are set at between 1.2 kV and 2 kV; the surface of the housing 16 immediately adjacent to the entrance to the second passageway 22, set at approximately 3.5 kV; and the second passageway 22 set at a slightly greater charge of about 4 kV (both the surface of the housing 16 and the second passageway 22 oppositely charged from charge of the source 150). The delta voltage ranges from between about 4 to 6 kV.

What is claimed is:

1. An apparatus for converting a solute sample into ionized molecules comprising:

a first passageway 110 having a center axis, an orifice for accepting a solute sample, an interior chamber 135 within which the solute sample is vaporized, and an exit 140 for discharging the vaporized molecules;

a point charge voltage source 150 having the point arranged adjacent to the first passageway exit 140;

an electrically conductive housing 16 connected to a second voltage source and having an opening 21 arranged adjacent to the first passageway exit wherein the electrospray formed by the point charge 150 is interposed between the point charge 150 and the housing 16;

a second passageway 22 arranged within the housing 16 adjacent to the opening 21 and connected to a third voltage source, the second passageway 22 having a center axis, an orifice 17 for receiving charged molecules attracted from the electrospray and an exit, wherein the center axis of the second passageway 22 is arranged in transverse relation to the center axis of the first passageway 110 such that the charged molecules in the electrospray move laterally through the opening 21 in the housing 16 and thereafter pass into the second passageway 22 under the influence of electrostatic attraction forces generated by the second and third voltages sources.

2. An apparatus for converting a liquid solute sample into ionized molecules, comprising:

(a) a first passageway having a center axis and an exit;

(b) a point charge voltage source arranged adjacent to said exit of said first passageway;

(c) a second passageway having a center axis; and (d) at least one additional voltage source connected to at least one of said passageways;

wherein said first passageway is capable of converting said liquid solute sample into vaporized molecules;

wherein said point charge voltage source is capable of converting said vaporized molecules into ionized molecules;

wherein said additional voltage source produces an electric field sufficient to move ionized molecules into said second passageway; and wherein said center axis of said first passageway is positioned transverse to said center axis of said second passageway at an angle of from about 75° to about 105°.

3. The apparatus of claim 2 wherein said angle is about 90°.

4. The apparatus of claim 2 further comprising a drying gas source.

* * * * *